(12) United States Patent
Puig Serrano et al.

(10) Patent No.: US 7,741,489 B2
(45) Date of Patent: Jun. 22, 2010

(54) PROCESS FOR THE SYNTHESIS OF SOLIFENACIN

(75) Inventors: Jordi Puig Serrano, Girona (ES); Pelayo Camps, Barcelona (ES)

(73) Assignee: Medichem S.A., Saint Joan Despi, Barcelona (ES)

( * ) Notice: Subject to any disclaimer, the term of this patent is extended or adjusted under 35 U.S.C. 154(b) by 270 days.

(21) Appl. No.: 12/079,814

(22) Filed: Mar. 28, 2008

(65) Prior Publication Data

US 2008/0242697 A1    Oct. 2, 2008

Related U.S. Application Data

(60) Provisional application No. 60/921,027, filed on Mar. 30, 2007, provisional application No. 60/928,199, filed on May 8, 2007.

(51) Int. Cl.
*C07D 453/02* (2006.01)
(52) U.S. Cl. .................................................. 546/137
(58) Field of Classification Search ................... 546/137
See application file for complete search history.

(56) References Cited

U.S. PATENT DOCUMENTS 6,017,927 A    1/2000 Takeuchi et al.

FOREIGN PATENT DOCUMENTS

EP    1714965    10/2006
EP    1757604    2/2007

OTHER PUBLICATIONS

Naito et al., Journal of Medicinal Chemistry (2005), 48(21), 6597-6606.*
U.S. Appl. No. 12/515,689, filed Aug. 4, 2009, Jordi Puig.
Naito et al., Synthesis and Antimuscarinic Properties of Quinuclidin-3-yl 1,2,3,4-Tetrahydroisoquinoline-2-carboxylate Derivatives as Novel Muscarinic Receptor Antagonists, *J. Med. Chem.* (2005) 48, 6597-6606.

* cited by examiner

*Primary Examiner*—D. Margaret Seaman
*Assistant Examiner*—Niloofar Rahmani
(74) *Attorney, Agent, or Firm*—Cohen Pontani Lieberman & Pavane LLP

(57) ABSTRACT

The present invention provides an improved synthetic strategy for the preparation of solifenacin and pharmaceutically acceptable salts thereof.

17 Claims, No Drawings

PROCESS FOR THE SYNTHESIS OF SOLIFENACIN

RELATED APPLICATIONS

This application claims priority from U.S. Provisional Patent Application Ser. Nos. 60/921,027, filed on Mar. 30, 2007, and 60/928,199, filed on May 8, 2007, the contents of which are incorporated herein by reference.

BACKGROUND OF THE INVENTION

Solifenacin succinate is a commercially marketed pharmaceutically active substance indicated for the treatment of overactive bladder with symptoms of urinary incontinence, urgency and high urinary frequency. Solifenacin succinate is the international common denomination for butanedioic acid compounded with (1S)-(3R)-1-azabicyclo[2.2.2]oct-3-yl-3, 4-dihydro-1-phenyl-2(1H)— isoquinolinecarboxylate (1:1), having an empirical formula of $C_{23}H_{26}N_2O_2 \cdot C_4H_6O_4$ and the structure represented in formula I given below.

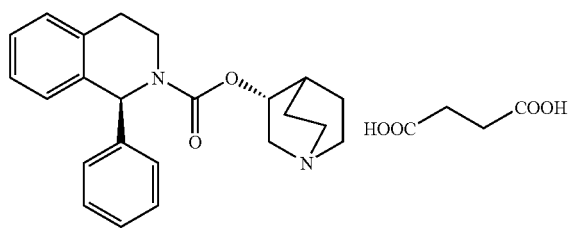

(I)

Solifenacin and its pharmaceutically acceptable salts are reported in U.S. Pat. No. 6,017,927 (the '927 patent).

The following Scheme 1 shows the synthetic routes disclosed in the '927 patent for the preparation of (1RS,3'RS)-solifenacin and (1S,3'RS)-solifenacin:

Scheme 1
Route A

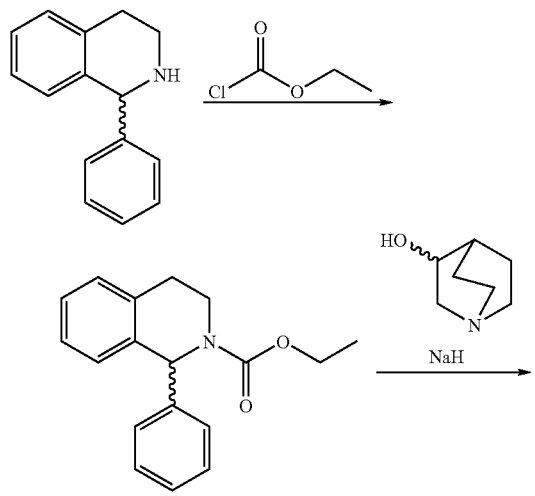

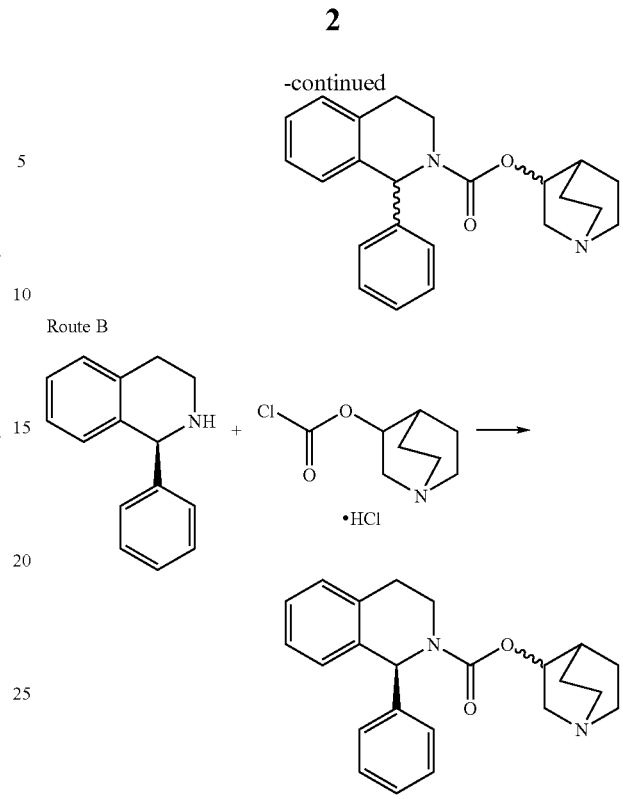

Route B

However, the processes described in the '927 patent for the preparation of solifenacin are not very efficient or suitable for industrial scale-up because they include laborious and costly work-ups. Further, since the ethyl carboxylate is used as the starting material in the process of Route A, ethanol is by-produced, and the by-produced ethanol launches a nucleophilic attack against solifenacin in the presence of a base. Thus, it is necessary to carry out the reaction while removing the ethanol from the reaction system, for example by the toluene azeotrope or the like, so that the control of the reaction is troublesome.

The following Scheme 2 shows the synthetic route disclosed in WO2005075474 for the preparation of solifenacin and solifenacin succinate:

Scheme 2

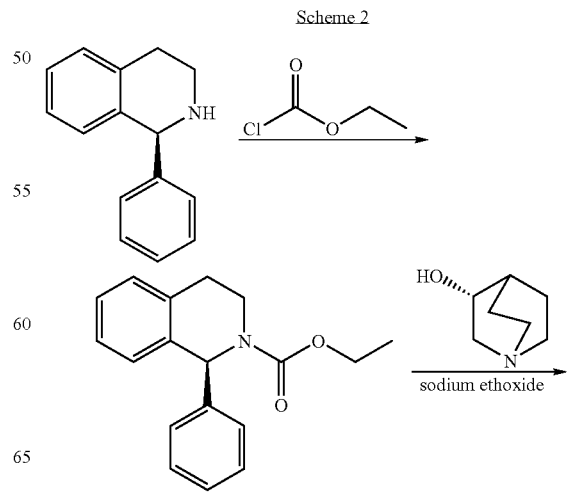

-continued

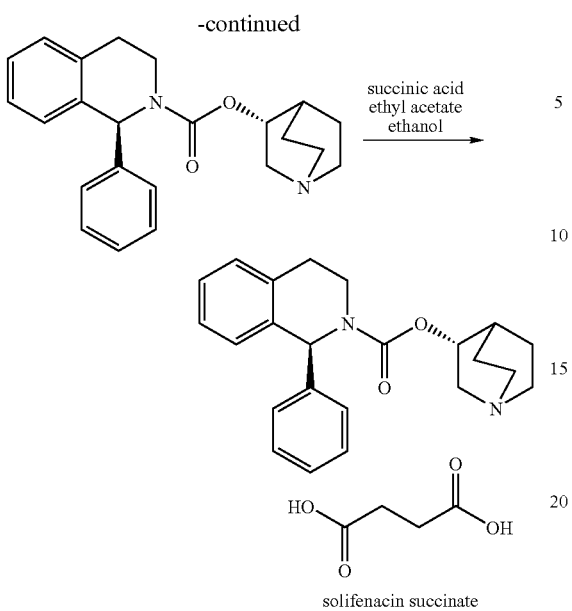

solifenacin succinate

However, the process described in this reference does not overcome the drawbacks associated with the state of the art processes.

Processes described in the prior art for the preparation of solifenacin and solifenacin succinate are not very efficient or suitable for industrial scale-up because they include expensive operations such as refluxing a mixture at high temperature for hours and laborious and costly work-ups including solvent exchanges and purification steps. So, there is a need for an improved and simplified process for the preparation of solifenacin and/or one of its salts that avoids the drawbacks of current state of the art processes.

SUMMARY OF THE INVENTION

The present invention discloses an improved synthetic strategy for the preparation of solifenacin and pharmaceutically acceptable salts thereof in a more efficient and simplified way than the processes described in the state of the art, i.e. makes use of milder reaction conditions, requires simpler experimental procedures, can be carried out with soft bases such as triethylamine, can be carried out at room temperature, and makes use of reduced work-ups. Further, the process of the present invention can be carried out via a one-pot procedure, i.e. without the need of isolating the intermediate compounds, which is very practical for scale-up production, especially in terms of operating efficiency. In addition, the process of the present invention affords solifenacin succinate with high yields. So, the process of the invention is cost-effective and well suited for industrial production.

DETAILED DESCRIPTION OF THE PREFERRED EMBODIMENTS

It is noted that use of the term solifenacin is intended to encompass the enantiopure form thereof, i.e. (1S,3'R)-solifenacin, whereas (1RS,3'RS)-solifenacin, and (1S,3'RS)-solifenacin are intended to encompass racemic mixtures of solifenacin, and (1R,3'R)-solifenacin, (1S,3'S)-solifenacin, and (1R,3'S)-solifenacin are intended to encompass enantiomeric derivatives of solifenacin.

The present invention discloses an improved synthetic strategy for the preparation of solifenacin and pharmaceutically acceptable salts thereof in a more efficient and simplified way than the processes described in the state of the art, i.e. makes use of milder reaction conditions, requires simpler experimental procedures, can be carried out with soft bases such as triethylamine, can be carried out at room temperature, and makes use of reduced work-ups. Further, the process of the present invention can be carried out via a one-pot procedure, i.e. without the need of isolating the intermediate compounds, which is very practical for scale-up production, especially in terms of operating efficiency. In addition, the process of the present invention affords solifenacin succinate with high yields. So, the process of the invention is cost-effective and well suited for industrial production.

Accordingly, a first aspect of the present invention relates to a process for obtaining solifenacin, or a pharmaceutically acceptable acid addition salt, made according to the process outlined in the following scheme 3.

Scheme 3

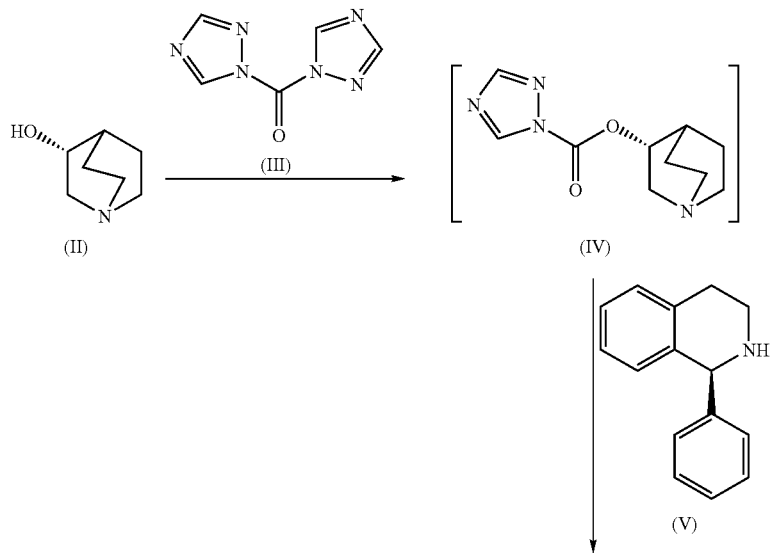

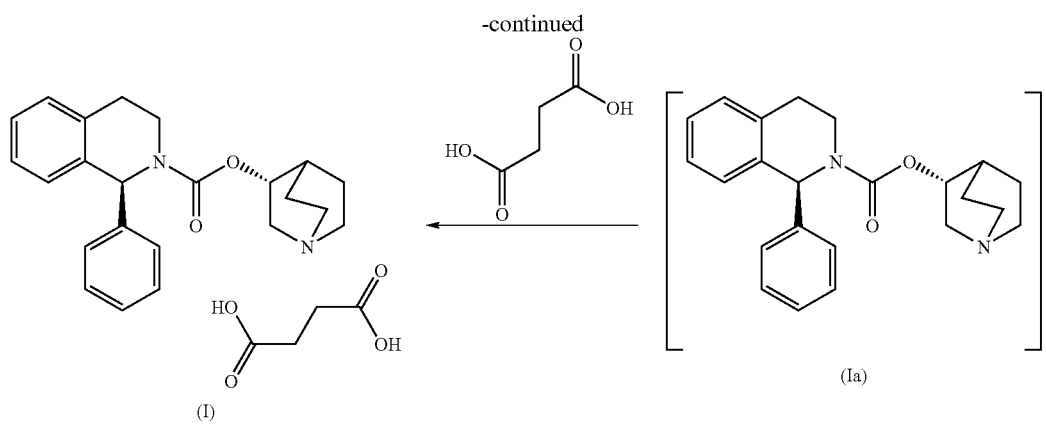

According to this process, (3R)-3-quinuclidinol, compound (II), is activated by reaction with bis-[1H-1,2,4-triazol-1-yl]-methanone (also named as 1,1-carbonyl-di-(1,2,4-triazole) and referred to in this document as CDT), compound (III), to form the corresponding carbamate that is not isolated. Suitable solvents for carrying out this reaction are ester solvents such as isopropyl acetate, ether solvents such as tetrahydrofuran and aromatic hydrocarbons such as toluene. The reaction can be carried out at room temperature (about 20-25° C.) and is completed in about 2 hours.

To the solution thus obtained, is added a solution of (S)-1-phenyl-1,2,3,4-tetrahydroisoquinoline, compound (V), in the same solvent used in the prior step and the resulting mixture is aged between 1 to 20 hours. The reaction temperature can range from 0° C. to the refluxing temperature of the solvent.

The suspension thus obtained is washed with water (the suspension disappears and two clear layers are obtained) and the layers are separated. The organic layer is washed again with a solution of water and sodium hydrogen carbonate. Alternatively, aqueous ammonium chloride can also be used. The organic layer that contains solifenacin base can be optionally dried by conventional means such as treatment with anhydrous sodium sulphate.

In a separate vessel, succinic acid is treated with acetone and heated to reflux. While maintaining the reflux, the solution of solifenacin base in the ester solvent is added. Once the addition is completed, the solution is cooled to room temperature and the solifenacin succinate precipitates out. The solid is isolated by filtration and dried by conventional means.

It will be apparent to those skilled in the art that various modifications and variations can be made in the present invention and specific examples provided herein without departing from the spirit or scope of the invention. Thus, it is intended that the present invention covers the modifications and variations of this invention that come within the scope of any claims and their equivalents.

SPECIFIC EXAMPLES

The following examples are for illustrative purposes only and are not intended, nor should they be interpreted, to limit the scope of the invention.

The following HPLC methods were used to determine the purity of the reactants and the solifenacin succinate product. The process as described in Examples 1 and 2 refer to the HPLC methods used as HPLC method 1 to 4.

General Experimental Conditions:

i) HPLC Method 1 (Chiral)

The chromatographic separation was carried out in a Chiralcel OD-H, 5 μm, 250×4.6 mm I.D column; at 45° C.

The mobile phase was prepared by mixing 975 volumes of n-hexane, 25 volumes of 2-propanol and 2 volumes of diethylamine.

The chromatograph was equipped with a 235 nm detector and the flow rate was 1.0 ml per minute. The test samples was prepared dissolving 200 mg of the sample in 2 ml of chloroform, adding 3 ml of benzoic anhydride solution prepared by dissolving 4 g of benzoic anhydride in 10 ml of chloroform and stirring for 20 min. at room temperature. Then was added 4 ml of 1 M HCl and stirred again. Then the aqueous part was extracted twice with 2 ml of chloroform and then added 4 ml of saturated potassium carbonate solution and 3 ml of n-hexane. This extract of the organic phase was dried over sodium sulphate and 50 μl part was injected.

ii) HPLC Method 2 (Chiral)

The chromatographic separation was carried out in a Chiralcel OD-H, 5 μm, 250×4.6 mm I.D column; at 40° C.

The mobile phase was prepared by mixing 500 volumes of n-hexane with 8 volumes of isopropanol and 1 volume of diethylamine.

The chromatograph was equipped with a 230 nm detector and the flow rate was 1.0 ml per minute. 10 μl of the test samples prepared by dissolving the appropriate amount of sample to obtain 20 mg per ml of a mixture of n-hexane/isopropanol/diethylamine (50:50:0.2 v/v/v) were injected.

iii) HPLC Method 3

The chromatographic separation was carried out in a Luna C18(2), 5 μm, 250×4.6 mm I.D column with a guard column; at room temperature (20-25° C.).

The mobile phase A was a buffer which was prepared from 1.23 g of ammonium acetate and dissolving it in 1000 ml of water and adjusting to pH=7.0 with ammonium hydroxide or acetic acid. This mobile phase was mixed and filtered through 0.22 μm nylon filter under vacuum.

The mobile phase B was acetonitrile.

The chromatograph was programmed as follows:

Initial 0-2 min. isocratic 55% mobile phase A, 2-60 min. linear gradient to 35% mobile phase A, 60-70 min. isocratic 35% mobile phase A, 70-75 min. linear gradient to 55% mobile phase A and 75-80 min. equilibration to 55% mobile phase A.

The chromatograph was equipped with a 220 nm detector and the flow rate was 1.0 ml per minute. 10 μl of the test samples prepared dissolving the appropriate amount of sample to obtain 5 mg per ml of a mixture of mobile phase A/mobile phase B (1:1) were injected.

iv) HPLC Method 4 (Chiral)

The chromatographic separation was carried out in a Chiralpak AD-H, 5 µm, 250×4.6 mm I.D column; at 45° C.

The mobile phase was prepared by mixing 950 volumes of n-hexane, 50 volumes of 2-propanol, 10 volumes of ethanol and 1 volume of diethylamine.

The chromatograph was equipped with a 225 nm detector and the flow rate was 1.4 ml per minute. 20 µl of the test samples prepared dissolving the appropriate amount of sample to obtain 20 mg per ml of a mixture of n-hexane/2-propanol/diethylamine (50:50:0.3 v/v/v) were injected.

Example 1

Into a 1 liter reaction vessel equipped with mechanical stirring, heating system, reflux condenser, addition funnel and innertized with nitrogen were charged: 29.47 g of bis-[1H-1,2,4-triazol-1-yl]-methanone (also named as 1,1-carbonyl-di-(1,2,4-triazole, 0.1676 mol, 93% purity) and 73 ml of isopropyl acetate. The mixture was stirred to homogenize and 21.31 g (0.1676 mol) of (R)-quinuclidin-3-ol [HPLC (method 1) purity: 96.03%, enantiomeric excess by HPLC (method 1)=99.26%] was added stepwise. 39.9 ml of Triethylamine (0.2863 mol) were also added and the mixture was stirred at room temperature for about 2 hours. At this point, a solution consisting of 29.22 g (0.1396 mol) of (S)-1-phenyl-1,2,3,4-tetrahydroisoquinoline [HPLC (method 2) purity: 97.81%, enantiomeric excess by HPLC (method 2)=97.80%] and 204 ml of isopropyl acetate was added stepwise and aged for 4 hours at reflux.

The resulting mixture was cooled down and washed with 170 ml of saturated aqueous ammonium chloride solution. The phases were separated and the aqueous phase was discarded. The organic phase was washed with 175 ml of a 10% aqueous solution of potassium bicarbonate. Again, after separating the phases, the aqueous one was discarded. The organic phase was labelled as solution A.

Into a 1 liter reaction vessel equipped with mechanical stirring, heating system, reflux condenser, addition funnel and innertized with nitrogen were charged: 21.44 g of succinic acid and 405 ml of acetone. The mixture was heated up to reflux to complete dissolution. Solution A was added stepwise while heating. Once the addition was over, the mixture is refluxed for an additional ½ hour and let to cool down. Precipitation of a white solid (solifenacin succinate) was observed. The solid was collected by filtration and dried at 40° C. in a vacuum oven to obtain 58.92 gram of the desired product (Yield: 87.89%, Assay: 101.5%; HPLC (method 3) purity: 99.61% area percent, optical purity, HPLC (method 4): (S,R) (Solifenacin succinate): 99.93%; (R,R): 0.03%; (S,S): 0.04%; (R,S): not detected, area percent). Particle Size: D(v,0.1)=6.5; D(v,0.5)=21.5; D(v,0.9)=43.6.

The solid thus obtained can be optionally dissolved in methanol in order to filter insoluble particles and precipitated from either:

(a) a mixture of methanol and acetone, optionally distilling methanol or acetone/methanol and adding an additional amount of succinic acid to further improve the yield, or (b) acetone, distilling methanol or acetone/methanol and optionally adding and additional amount of succinic acid to further improve the yield.

Example 2

Into a 28 liters capacity, cylindrical, glassy reactor equipped with an anchor impeller and purged with nitrogen, 606.80 g (99.10% essay, 3.33 mol) of 1,1'-carbonyl-di-(1,2,3,4-triazole) (CDT) and 1.2 liters of isopropyl acetate were charged. The mixture was stirred to homogenize and 425 g (3.34 mol) of quinuclidin-3-ol were added. Then, 577 g (790 ml, 5.70 mol) of triethylamine were added, washing the addition funnel with 259 ml of isopropyl acetate.

The mixture was heated up to reflux and a solution consisting on 581 g (2.78 mol) of 1(S)-1-phenyl-1,2,3,4-tetrahydroisoquinoline in 4076 ml of isopropyl acetate we added, washing the addition device with 291 ml of the same solvent.

The mixture was heated and refluxed for 4 h and cooled down to 0-5° C., at which point a saturated solution of ammonium chloride (prepared from 1800 g of ammonium chloride and 4610 g of water) was added. Temperature was kept at about 0-5° C. in the beginning of the addition. 1.164 kg of water was added in order to dissolve the eventual precipitation of salts.

The aqueous phase was rejected and the organic phase washed with a 10% solution of potassium bicarbonate (3.84 kg of water and 0.38 kg of potassium bicarbonate). After decantation the aqueous phase was rejected. The organic phase was transferred into an addition funnel (solution A). Into the cylindrical reactor, 427 g (3.62 mol) of succinic acid and 7.7 L of acetone were added. The mixture was heated up to reflux to complete dissolution, and solution A was added drop-wise.

After a partial distillation (5.7 kg of solvent mixture was distilled out), 3.5 L of acetone were added, heated up to reflux again to dissolve and cooled down to 0-5° C., aged for 2 h at this temperature and the solid filtered by filtration.

The wet solid was dissolved in methanol (3.8 liters) and heated up to 35° C. to remove mechanical particles. 1.30 kg of methanol were distilled out, 8.02 kg of acetone were charged instead, 10.2 L of solvent mixture were further distilled and 8.02 kg of acetone charged and, finally, 3.81 L of solvent distilled out. After stirring the resulting mixture at 0-5° C. for about 3 h, the solid was collected by filtration, yielding 1019 g of solifenacin succinate. Drying conditions: 40° C. in a vacuum over until constant weight. Yield: 76.38%; Assay: 99.5%; HPLC (method 3) purity: 99.96% area percent; optical purity, HPLC (method 4): (S,R) (Solifenacin succinate): 99.98% area percent, (R,R): not detected; (S,S): 0.02%; (R,S): not detected). Particle Size: D(v,0.1)=7.8; D(v,0.5)=23.0; D(v,0.9)=44.5. Particle size after milling and sieving: D(v,0.1)=7.7; D(v,0.5)=23.6; D(v,0.9)=46.1.

We claim:
1. A process for preparing solifenacin base (Ia),

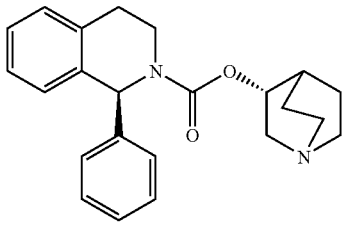

said process comprising:
(i) reacting (3R)-3-quinuclidinol (II),

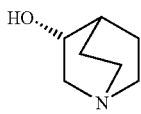

with 1,1-carbonyl-di-(1,2,4-triazole) (III),

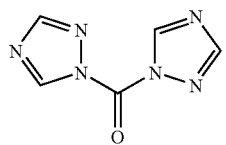

in an organic solvent to obtain a mixture, and
(ii) combining the mixture of step (i) with (S)-1-phenyl-1,2,3,4-tetrahydroisoquinoline (V),

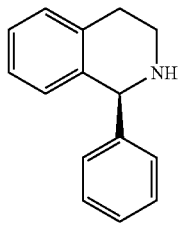

in the presence of a base to obtain solifenacin base.

2. The process of claim 1, further comprising the step of isolating the solifenacin base.

3. The process of claim 1, further comprising converting the solifenacin base into one of its pharmaceutically acceptable salts.

4. The process of claim 1, wherein the organic solvent is an ester solvent, an ether solvent, an aromatic hydrocarbon solvent, or a mixture thereof.

5. The process of claim 4, wherein the organic solvent is isopropyl acetate, tetrahydrofuran, 2-methyltetrahydrofuran, toluene, xylene, or a mixture thereof.

6. The process of claim 5, wherein the organic solvent is isopropyl acetate.

7. The process of claim 1, wherein the base of step (ii) is an inorganic or an organic base.

8. The process of claim 7, wherein the base of step (ii) is a hydride base, a $C_1$-$C_{10}$ alkoxide base, or an amine base.

9. The process of claim 8, wherein the base of step (ii) is triethylamine.

10. The process of claim 3, wherein the process comprises converting solifenacin base into solifenacin succinate salt (I).

11. The process of claim 10, further comprising purifying the solifenacin succinate salt, the purification process comprising:
(i) combining solifenacin succinate with a $C_1$-$C_4$ alcohol to obtain a solution,
(ii) adding a ketone solvent,
(iii) distilling off the solvent to further concentrate the mixture, and
(iv) isolating solifenacin succinate from the mixture.

12. The process of claim 11, wherein the purification process further comprises one or both of the following steps after step (i) of combining solifenacin succinate with a $C_1$-$C_4$ alcohol:
(a) filtering the solution of step (i) to remove isoluble particles from the solution, and
(b) partially distilling all the solvent to concentrate the mixture.

13. The process of claim 11, wherein the $C_1$-$C_4$ alcohol is ethanol, methanol, or a mixture thereof.

14. The process of claim 13, wherein the $C_1$-$C_4$ alcohol is methanol.

15. The process of claim 11, wherein the ketone solvent is acetone, methyl ethyl ketone (MEK), or a mixture thereof.

16. The process of claim 15, wherein the ketone solvent is acetone.

17. The process of claim 11, further comprising milling and sieving the obtained solifenacin succinate salt.

* * * * *